(12) United States Patent
Kim et al.

(10) Patent No.: US 11,428,629 B2
(45) Date of Patent: Aug. 30, 2022

(54) INTESTINAL MICROORGANISM DETECTION SYSTEM

(71) Applicant: The Wave Talk, Inc., Daejeon (KR)

(72) Inventors: Young Dug Kim, Seongnam-si (KR); Nam Kyun Kim, Seongnam-si (KR)

(73) Assignee: The Wave Talk, Inc., Daejeon (KR)

( * ) Notice: Subject to any disclaimer, the term of this patent is extended or adjusted under 35 U.S.C. 154(b) by 300 days.

(21) Appl. No.: 16/770,238

(22) PCT Filed: Dec. 7, 2018

(86) PCT No.: PCT/KR2018/015478
§ 371 (c)(1),
(2) Date: Jun. 5, 2020

(87) PCT Pub. No.: WO2019/112359
PCT Pub. Date: Jun. 13, 2019

(65) Prior Publication Data
US 2021/0164899 A1    Jun. 3, 2021

(30) Foreign Application Priority Data
Dec. 8, 2017 (KR) .......................... 10-2017-0168482

(51) Int. Cl.
*G01N 21/55* (2014.01)
*C12Q 1/24* (2006.01)
(Continued)

(52) U.S. Cl.
CPC .............. *G01N 21/55* (2013.01); *C12Q 1/24* (2013.01); *G01N 1/38* (2013.01); *G01N 33/483* (2013.01)

(58) Field of Classification Search
CPC ........ G01N 21/55; G01N 1/38; G01N 33/483; G01N 2021/479; G01N 21/4788;
(Continued)

(56) References Cited

U.S. PATENT DOCUMENTS

2018/0298419 A1* 10/2018 Ronsick .................. C12Q 1/24

FOREIGN PATENT DOCUMENTS

| JP | 11-072492 | 3/1999 |
|----|-----------|--------|
| JP | 2002-071678 | 3/2002 |

(Continued)

OTHER PUBLICATIONS

International Search Report and Written Opinion for PCT/KR2018/015478, dated Mar. 8, 2019 (w/English translation of International Search Report).

(Continued)

*Primary Examiner* — Jennifer Wecker
*Assistant Examiner* — Oyeleye Alexander Alabi
(74) *Attorney, Agent, or Firm* — Klarquist Sparkman, LLP

(57) ABSTRACT

An embodiment of the present disclosure provides an intestinal microorganism detection system including: a feces collection unit configured to collect the feces of a user: a storage unit including a plurality of accommodation units configured to accommodate a fecal sample, the fecal sample being formed by mixing the feces collected by the feces collection unit with fluid; a sensor unit configured to detect a microorganism in the fecal sample accommodated in each of the plurality of accommodation units and generate first information; and a control unit configured to estimate, on the basis of the generated first information, the type of intestinal microorganism present in the user and a concentration thereof, wherein the plurality of accommodation units are respectively exposed to different environmental conditions.

17 Claims, 10 Drawing Sheets

(51) Int. Cl.
*G01N 1/38* (2006.01)
*G01N 33/483* (2006.01)

(58) Field of Classification Search
CPC ........ G01N 21/84; G01N 21/41; G01N 21/47;
G01N 33/4833; G01N 2021/4735; C12Q
1/24
See application file for complete search history.

(56) References Cited

FOREIGN PATENT DOCUMENTS

| | | |
|---|---|---|
| JP | 2009-204598 | 9/2009 |
| JP | 2014-194412 | 10/2014 |
| KR | 10-2012-0089769 | 8/2012 |
| WO | WO2017/086719 | 5/2017 |

OTHER PUBLICATIONS

Office Action for Korean Application No. 10-2017-0168482, dated Jul. 4, 2022 (w/English translation).

* cited by examiner

INTESTINAL MICROORGANISM DETECTION SYSTEM

CROSS REFERENCE TO RELATED APPLICATIONS

This is the U.S. National Stage of International Application No. PCT/KR2018/015478, filed Dec. 7, 2018, which in turn claims the benefit of Korean Patent Application No 10-2017-0168482, filed Dec. 8, 2017, which applications are incorporated herein in their entirety.

TECHNICAL FIELD

Embodiments of the present disclosure relate to an intestinal microorganism detection system.

BACKGROUND ART

Recently, research has revealed that microorganisms, which inhabit our bodies, have a great impact on the human body, and thus, studies on intestinal microorganisms are ongoing, such as the organization of "the International Human Microbiome Consortium (IHMC)," in order to analyze and share the genetic information of microorganisms. Various microorganisms in the human body are known to affect biometabolic regulation and digestive abilities or various diseases, and to influence all functions of the human body, such as genetic modification according to environmental changes and the process of passing onto the next generation. In particular, various metabolic and immune diseases related to allergies, rhinitis, atopy, and obesity, enteritis, heart disease, and the like have been reported to be related to these intestinal microorganisms.

Methods of measuring bacteria and microorganisms include microbial culture methods, mass spectrometry, nuclear magnetic resonance techniques, and the like. In the case of microbial culture methods, mass spectrometry, and nuclear magnetic resonance techniques, specific types of bacteria can be accurately measured, but sample preparation takes a long time, and expensive, precise and complicated equipment is required. Therefore, there is a need for a method of rapidly and accurately examining the presence of pathogenic microorganisms in the human body in daily life.

DESCRIPTION OF EMBODIMENTS

Technical Problem

To address the above-described problems and/or limitations, an objective of the present disclosure is to provide a system capable of detecting intestinal microorganisms in real time.

Solution to Problem

According to an embodiment of the present disclosure, an intestinal microorganism detection system includes a feces collection unit configured to collect the feces of a user, a storage unit including a plurality of accommodation units configured to accommodate a fecal sample, the fecal sample being formed by mixing the feces collected by the feces collection unit with fluid, a sensor unit configured to detect a microorganism in the fecal sample accommodated in each of the plurality of accommodation units and generate first information, and a control unit configured to estimate, on the basis of the generated first information, the type of intestinal microorganism present in the user and a concentration thereof, wherein the plurality of accommodation units are respectively exposed to different environmental conditions.

In one embodiment of the present disclosure, the different environmental conditions may be conditions in which it is possible to distinguish a predetermined target microorganism and microorganisms other than the target microorganism.

In one embodiment of the present disclosure, the different environmental conditions may be conditions for the survival or proliferation of predetermined different target microorganisms in each of the plurality of accommodation units.

In one embodiment of the present disclosure, the environmental condition may be a pH condition, a carbon dioxide concentration condition, an oxygen concentration condition, an alcohol concentration condition, a temperature condition, a humidity condition, an antibiotic condition, a microorganism-specific marker condition, or a combination thereof.

In one embodiment of the present disclosure, each of the plurality of accommodation units may accommodate the fecal sample that is distributed in certain amounts.

In one embodiment of the present disclosure, the feces collection unit may include a feces accommodation unit configured to accommodate the feces of a user, a transfer pipe that connects the feces accommodation unit to the storage unit, and a fluid supply unit configured to supply the fluid to the transfer pipe.

In one embodiment of the present disclosure, the feces collection unit may further include a weight measurement sensor, a moisture content measurement sensor, an occult blood measurement sensor, or a combination thereof.

In one embodiment of the present disclosure, the storage unit may include a main pipe connected to the transfer pipe, a plurality of sub-pipes that connect the main pipe to each of the plurality of accommodation units, an environment control unit configured to control an environmental condition of each of the plurality of accommodation units, and a drainage control unit configured to control discharge of the fecal sample accommodated in each of the plurality of accommodation units.

In one embodiment of the present disclosure, the storage unit may further include a filter unit provided in the main pipe, and configured to filter substances of certain sizes or larger in the fecal sample and transfer the filtrate to the sub-pipes.

In one embodiment of the present disclosure, the sensor unit may detect the presence of a microorganism in the fecal sample accommodated in each accommodation unit by using waves.

In one embodiment of the present disclosure, the sensor unit may include a wave source configured to emit waves towards the fecal sample accommodated in each accommodation unit, and a detection unit configured to detect, at a predetermined time point, a signal generated by reflection, refraction, diffraction, scattering, dispersion, or interference of the emitted waves in the fecal sample.

In one embodiment of the present disclosure, each of the plurality of accommodation units may include a multiple scattering amplification region for amplifying the number of multiple scattering events in each accommodation unit of waves, the waves being incident onto each accommodation unit.

In one embodiment of the present disclosure, at least a portion of the multiple scattering amplification region may reflect, into the fecal sample, at least some of the waves emitted from the fecal sample to thereby amplify the number of multiple scattering events in the fecal sample.

In one embodiment of the present disclosure, at least a portion of the multiple scattering amplification region may include a reflection region that reflects, into the fecal sample, at least some of the waves emitted from the fecal sample.

In one embodiment of the present disclosure, the sensor unit may include a wave source configured to emit waves towards the fecal sample accommodated in each accommodation unit, and at least one detection unit configured to detect, every predetermined time point, a wave speckle generated by multiple scattering of the emitted waves in each accommodation unit, and the control unit may acquire a temporal correlation of the detected wave speckle by using the detected wave speckle, and estimate, on the basis of the acquired temporal correlation, the type of intestinal microorganism present in the fecal sample accommodated in each of the plurality of accommodation units and a concentration thereof.

In one embodiment of the present disclosure, the estimation may include estimating in real time, on the basis of the acquired temporal correlation, the type of intestinal microorganism present in the fecal sample accommodated in each of the plurality of accommodation units and a concentration thereof.

In one embodiment of the present disclosure, the temporal correlation may include a difference between first image information of the wave speckle detected at a first time point and second image information of the wave speckle detected at a second time point different from the first time point.

In one embodiment of the present disclosure, the first image information and the second image information may include at least any one of pattern information of the wave speckle and intensity information of the waves.

Other aspects, features, and advantages will become apparent from the accompanying drawings, claims, and the detailed description.

Advantageous Effects of Disclosure

An intestinal microorganism detection system according to embodiments of the present disclosure can rapidly estimate the types of intestinal microorganisms and concentrations thereof at low cost.

MODE OF DISCLOSURE

Figure 1:
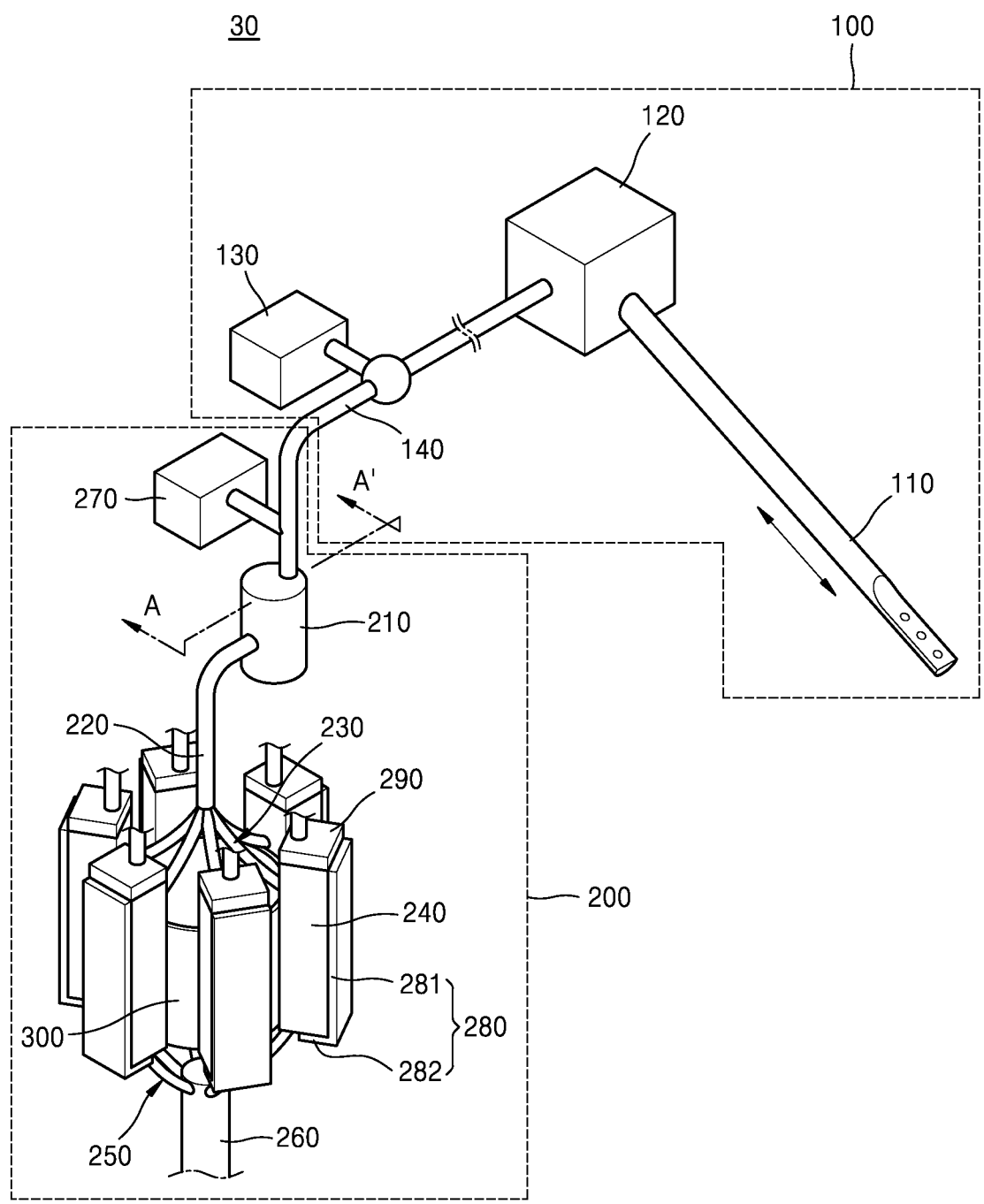
FIG. 1 is an exemplary view of a feces collection unit, a storage unit, and a sensor unit of an intestinal microorganism detection system according to an embodiment of the present disclosure, realized as an experimental apparatus.

Hereinafter, the following embodiments will be described in detail with reference to the accompanying drawings, and in description with reference to the drawings, like reference numerals denote like or corresponding elements and a detailed description thereof will be provided only once.

As the present embodiments allow for various changes, particular embodiments will be illustrated in the drawings and described in detail in the written description. Effects and features of the present embodiments, and methods of achieving the same will become apparent from the following detailed description with reference to the accompanying drawings. However, the present embodiments are not limited to the embodiments set forth herein, and may be embodied in many different forms.

In the following embodiments, terms such as first and second are not used for the purpose of limitation, but are used to distinguish one element from another.

In the following embodiments, an expression in the singular encompasses the expression in the plural, unless context clearly indicates otherwise.

In the following embodiments, terms such as including or having are intended to indicate the existence of features or components described in the specification, and are not intended to preclude the possibility that one or more other features or components may be added.

In the following embodiments, when a portion such as a unit, a region, or a component is referred to as being "above" or "on" another portion, this includes not only the case where the portion is directly on the other portion but also the case where another unit, another region, another component, or the like is present between the two portions.

In the following embodiments, terms such as "connected" or "coupled" do not necessarily mean a direct and/or fixed connection or coupling between two members unless the context clearly dictates otherwise, and another intervening member may exist between the two members.

These terms are intended to indicate the existence of the features or components disclosed in the specification, and are not intended to preclude the possibility that one or more other features or components may be added.

In the drawings, for convenience of description, the sizes of components may be more or less exaggeratedly shown. For example, the size and thickness of each of a plurality of elements shown in the drawings are arbitrarily represented for convenience of description, and the following embodiments are not necessarily limited by the illustrations.

Figure 2:
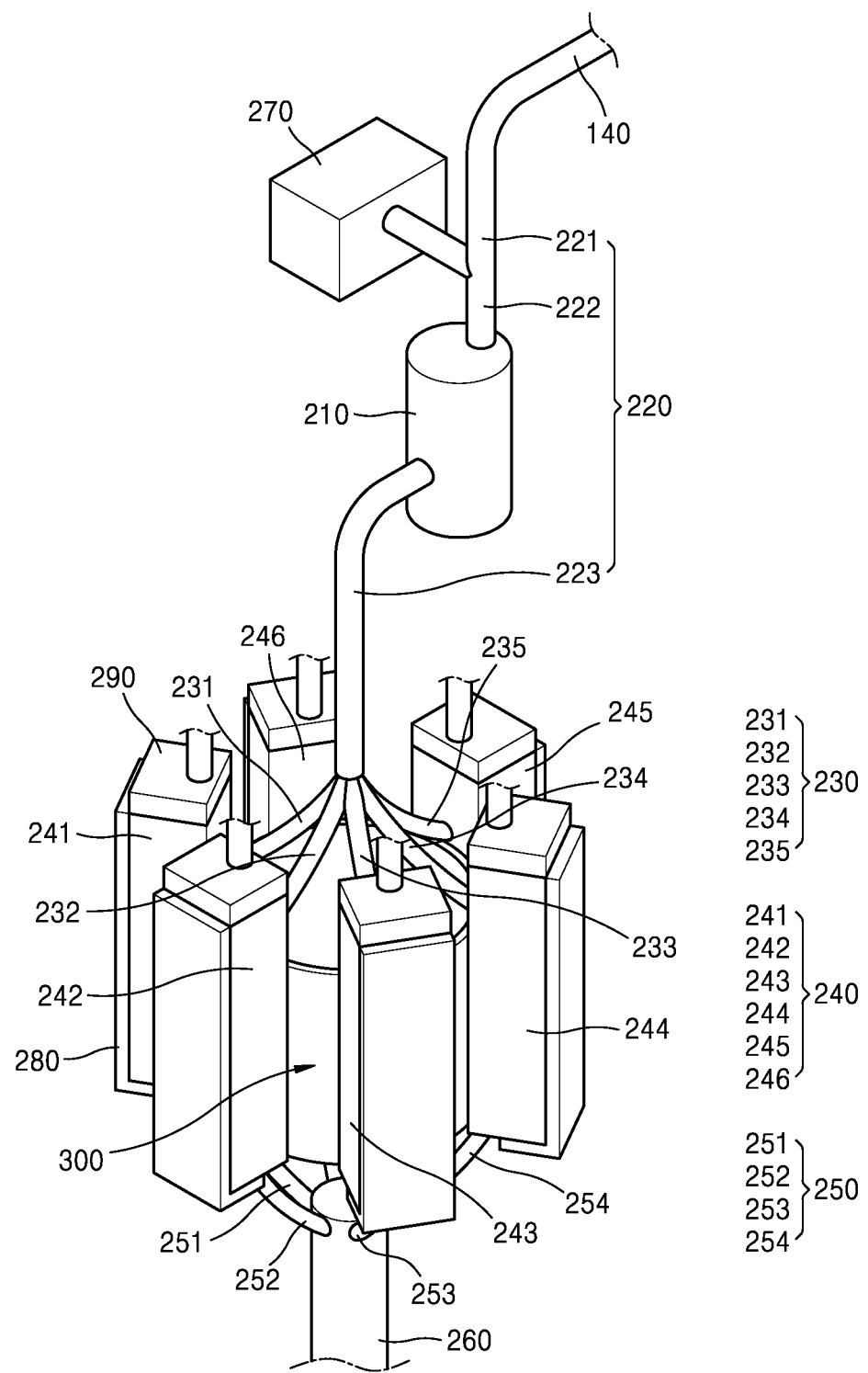
FIG. 2 is an exemplary view of a storage unit and a sensor unit of an intestinal microorganism detection system according to an embodiment of the present disclosure, realized as an experimental apparatus.
Figure 3:
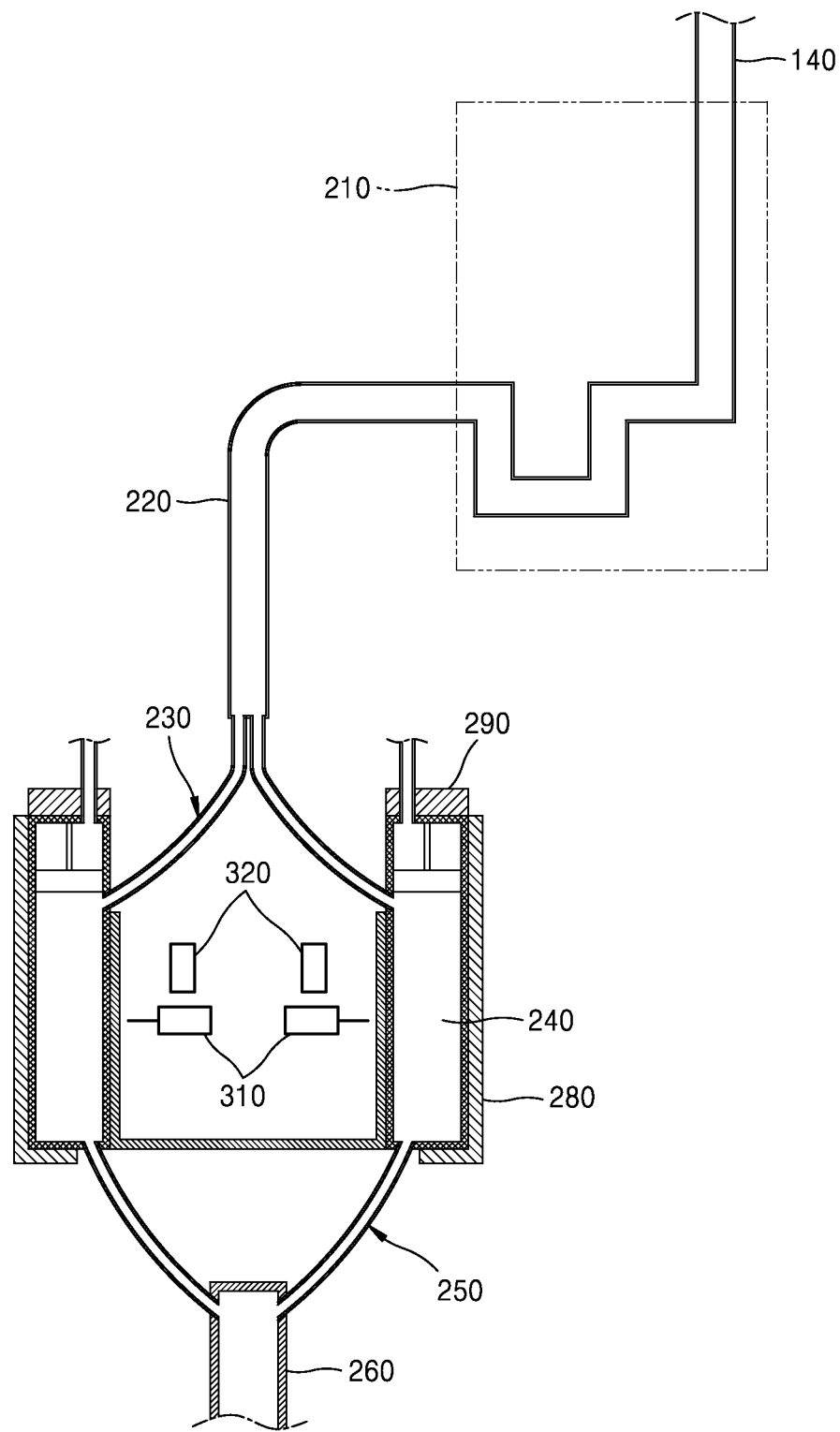
FIG. 3 is a cross-sectional view of an accommodation unit and a sensor unit of an intestinal microorganism detection system according to an embodiment of the present disclosure.

FIG. 1 is an exemplary view of a feces collection unit, a storage unit, and a sensor unit of an intestinal microorganism detection system according to an embodiment of the present disclosure that are realized as an experimental apparatus. FIG. 2 is an exemplary view of a storage unit and a sensor unit of an intestinal microorganism detection system according to an embodiment of the present disclosure that are realized as an experimental apparatus. FIG. 3 is a cross-sectional view of an accommodation unit and a sensor unit of an intestinal microorganism detection system according to an embodiment of the present disclosure.

A feces collection unit 100 may include a feces accommodation unit 110, a suction pump unit 120, a fluid supply unit 130, and a transfer pipe 140.

The feces accommodation unit 110 collects and accommodates the feces of a user. In addition, the feces accommodation unit 110 may have an end with a concave bar-type shape, but the present disclosure is not limited thereto. The feces accommodation unit 110 may further include a weight measurement sensor (not shown), a moisture content measurement sensor (not shown), an occult blood measurement sensor (not shown), or a combination thereof. The feces accommodation unit 110 may measure moisture content, weight, or the presence or absence of bleeding, before detection of microorganisms present in the feces of a user.

Figure 4:
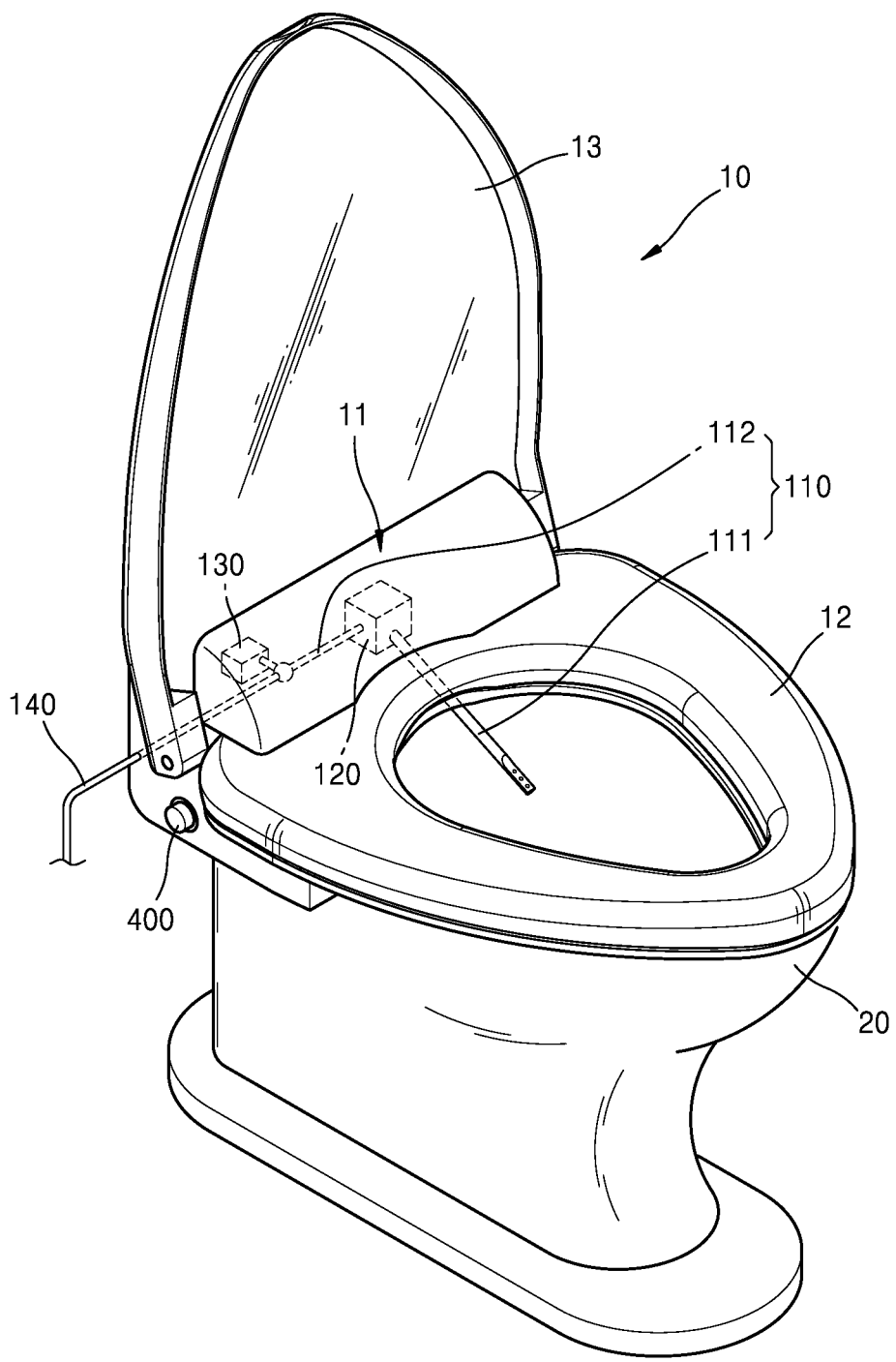
FIG. 4 is an exemplary view of an intestinal microorganism detection system according to an embodiment of the present disclosure, implemented in an applied apparatus.

The suction pump unit 120 transfers the feces accommodated in the feces accommodation unit 110 to the transfer pipe 140. The suction pump unit 120 provides a flow force to move feces, fluid, or a fecal sample. Referring to FIG. 1, for example, the suction pump unit 120 may move the feces itself from the feces accommodation unit 110 towards the suction pump unit 120 by suction force. Specifically, the suction pump unit 120 may transfer the feces accommodated in the feces accommodation unit 110 to the transfer pipe 140 by using a suction method. Referring to FIG. 4, for example, in other embodiments, the feces accommodation unit 110 may include a suction nozzle 111 having one end exposed outside of a main body portion 11 and an ejection nozzle 112 connected to the transfer pipe 140. In addition, the suction pump unit 120 may be connected between the suction nozzle 111 and the ejection nozzle 112 and include an impeller (not shown) therein that rotates at a high speed. In addition, according to the high-speed rotation of the impeller, the feces accommodated in one end of the suction nozzle 111 may be transferred to the transfer pipe 140 via the ejection nozzle 112. In another embodiment, the suction pump unit 120 may transfer fluid supplied by the fluid supply unit 130 to the suction nozzle 111 having feces accommodated therein, allowing the collected feces to come into contact with the fluid, and then may transfer the feces in the fluid to the transfer pipe 140. In this case, the suction nozzle 111 may have positioned therein a pipe (not shown) that transfers fluid from the suction pump unit 120 to one end of the suction nozzle 111 and a pipe (not shown) that transfers feces in the fluid towards the suction pump unit 120 from the end of the suction nozzle 111. A method of transferring the feces accommodated in the feces accommodation unit 110 to the transfer pipe 140 is not limited to those as described above, and known methods capable of transferring a material along a pipe by pressure or using a driving motor are applicable.

The fluid supply unit 130 may supply fluid into the transfer pipe 140. The fluid discharged from the fluid supply unit 130 may be mixed with feces in the transfer pipe 140, thereby forming a fecal sample in the transfer pipe 140. Although not shown in the drawings, the fluid supply unit 130 may include a fluid storage tank (not shown) and a supply member, such as a hydraulic pump or a compressor (not shown), for supplying flow force to fluid accommodated in the fluid storage tank. Fluid may be unidirectional via the supply member and pass through the transfer pipe 140.

The transfer pipe 140 provides a path through which the collected feces is transferred from the feces accommodation unit 110 to a storage unit 200. That is, the transfer pipe 140 connects the feces accommodation unit 110 to the storage unit 200. In addition, one end of the transfer pipe 140 is connected to the fluid supply unit 130, and the fluid supply unit 130 discharges fluid towards the transfer pipe 140. In addition, the feces and the fluid discharged from the fluid supply unit 130 are mixed in the transfer pipe 140 and diluted to a predetermined ratio, thereby forming a fecal sample, and the formed fecal sample is transferred to the storage unit 200. A ratio of feces to fluid in the fecal sample may be determined by the weight of sensed feces, moisture content in the feces, or a combination thereof, or may be determined by detection sensitivity, detection accuracy, or a combination thereof of a sensor unit 300, which are previously set.

In this regard, the fluid may be a substance that enables microorganisms in feces to survive or proliferate, and is not limited as long as it is mixed with feces, allowing the feces to be uniformly mixed therein. The fluid may be, for example, phosphate buffered saline, a culture medium, deionized water, or a combination thereof.

The storage unit 200 may include a filter unit 210, a main pipe 220, a sub-pipe 230, an accommodation unit 240, a discharge pipe 250, a confluent pipe 260, a first drainage control unit 270, an environment control unit 280, and a second drainage control unit 290.

The main pipe 220 may connect the transfer pipe 140 to a plurality of sub-pipes 230, The fecal sample introduced via the transfer pipe 140 is transferred to the plurality of sub-pipes 230 via the main pipe 220. The plurality of sub-pipes 230 may be respectively connected to a plurality of accommodation units 240. The sub-pipe 230 may include a plurality of sub-pipes 230, and the accommodation unit 240 may include a plurality of accommodation units 240 to correspond thereto. For example, the sub-pipe 230 may include first, second, third, fourth, fifth, and sixth sub-pipes 231, 232, 233, 234, 235, and 236, and the accommodation unit 240 may include first, second, third, fourth, fifth, and sixth accommodation units 241, 242, 243, 243, 244, 245, and 246 to correspond thereto. In this regard, one end of the first sub-pipe 231 is connected to the main pipe 220, and another end thereof is connected to the first accommodation unit 241. One end of the second sub-pipe 232 is connected to the main pipe 220, and another end thereof is connected to the second accommodation unit 242. One end of the third sub-pipe 233 is connected to the main pipe 220, and another end thereof is connected to the third accommodation unit 243. One end of the fourth sub-pipe 234 is connected to the main pipe 220, and another end thereof is connected to the fourth accommodation unit 244. One end of the filth sub-pipe 235 is connected to the main pipe 220, and another end thereof is connected to the fifth accommodation unit 245. One end of the sixth sub-pipe 236 is connected to the main pipe 220, and another end thereof is connected to the sixth accommodation unit 246. The first, second, third, fourth, fifth, and sixth sub-pipes 231, 232, 233, 234, 235, and 236 and the first, second, third, fourth, fifth, and sixth accommodation units 241, 242, 243, 243, 244, 245, and 246 are one example selected for convenience of explanation, and the plurality of sub-pipes 230 and the plurality of accommodation units 240 may be applied in various numbers. The plurality of sub-pipes 230 may have the same shape and the same length. In this case, the fecal sample introduced via the main pipe 220 may be distributed in the same amount and introduced into the plurality of sub-pipes 230. Alternatively, the plurality of sub-pipes 230 may have different shapes and different lengths. In this case, the fecal sample introduced via the main pipe 220 may be distributed in different amounts and introduced into the plurality of sub-pipes 230. The shapes and lengths of the plurality of sub-pipes 230 may be determined by the type of target microorganism, which is a subject to be detected, or detection sensitivity, detection accuracy, or a combination thereof of the sensor unit 300, which are previously set.

The main pipe 220 may include a first main pipe 221 connected to the transfer pipe 140, a second main pipe 222 connected to the first main pipe 221, and a third main pipe 223 connected to the second main pipe 222 and the sub-pipe 230. The first drainage control unit 270 may be installed between the first main pipe 221 and the second main pipe 222, The first drainage control unit 270 may control a flow rate between the first and second main pipes 221 and 222. That is, the first drainage control unit 270 may connect or block the first main pipe 221 to or from the second main pipe 222. For example, the first drainage control unit 270 may have a valve shape. When the first and second main pipes 221 and 222 are blocked from each other, the fecal sample is collected in the first main pipe 221. The filter unit 210 may be installed between the second main pipe 222 and the third main pipe 223. The fecal sample introduced via the second main pipe 222 may be filtered by the lifter unit 210 and transferred to the third main pipe 223. The filter unit 210 is capable of filtering substances of certain sizes or larger in the fecal sample and may allow microorganisms to pass therethrough.

The fecal sample flows into the accommodation unit 240 via the sub-pipe 230.

Each of the plurality of accommodation units 240 may accommodate the fecal sample that is distributed in pre-set amounts. Each of the plurality of accommodation units 240 may accommodate the fecal sample that is distributed in certain amounts. The plurality of accommodation units 240 may be arranged apart from each other by a predetermined distance. The plurality of accommodation units 240 are respectively exposed to different environments by the environment control units 280.

The accommodation unit 240 may have installed therein the environment control unit 280 for controlling an internal environment condition of the accommodation unit 240. The environment condition may be a condition in which it is possible to distinguish a target microorganism from microorganisms other than the target microorganism. The environment condition may be a condition in which it is possible to differently control the survival or proliferative rate of the target microorganism and the survival or proliferative rates of microorganisms other than the target microorganism. The environment condition may be a condition that maintains or promotes the survival or proliferation of the target microorganism, and inhibits the survival or proliferation of or kills microorganisms other than the target microorganism, Conversely, the environment condition may be a condition that inhibits the survival or proliferation of the target microorganism or kills the same, while being capable of maintaining or promoting the survival or proliferation of microorganisms other than the target microorganism. Alternatively, the environment condition may be a condition capable of labeling only the target microorganism. That is, the environment control units 280 may be differently configured according to the type of target microorganism to be detected in each accommodation unit 240. These environment conditions may be previously set. The environment condition is not limited as long as it is a condition in which it is possible to distinguish a target microorganism from microorganisms other than the target microorganism, and may be, for example, a pH condition, a carbon dioxide concentration condition, an oxygen concentration condition, an alcohol concentration condition, a temperature condition, a humidity condition, an antibiotic condition, a microorganism-specific labeling condition, or a combination thereof. For example, the environment control unit 280 may include a heating/cooling device 281 installed to adjust the temperature inside the accommodation unit 240, a material supply device 282 for pH control which is installed to control pH inside the accommodation unit 240, a carbon dioxide supply device (not shown), an oxygen supply device (not shown), an alcohol supply device (not shown), a device (not shown) for supplying an antibiotic which allows a target microorganism to proliferate or survive, but inhibits the survival of microorganisms other than the target microorganism, a device (not shown) for supplying a target microorganism-specific marker (e.g., a fluorescent material, a phosphorescent material, a luminescent material, a radioactive material, a dye, and an antibody), a sterilization device (not shown), or a combination thereof. For example, the environment condition may be a medium containing a component that promotes the growth of a predetermined target microorganism or maintains the survival thereof, and at the same time, may be a medium containing a component that inhibits the growth of microorganisms other than the target microorganism. The environment control unit 280 may be installed on an inner and/or outer surface of the accommodation unit 240.

The target microorganism may include at least one intestinal microorganism. The target microorganisms may be different in size, shape, motility, anaerobicity/aerobicity, responsiveness to environmental conditions, for example, chemotaxis, phototaxis, thermotaxis, galvanotaxis, or magnetotaxis, or a combination thereof.

The target microorganism may be an indicator microorganism. The target microorganism may be an indicator microorganism, and may be an intestinal microorganism belonging to any phylum in the microbial classification system and a microorganism that represents any phylum. The target microorganism may be an intestinal microorganism, a pathogenic microorganism, or a combination thereof, which are frequently found in any phylum. The target microorganism may be a microorganism belonging to the phylum Bacteroidetes, Firmicutes, Actinobacteria, Proteobacteria, Verrucomicrobia, or Fusobacteria. The microorganism belonging to the phylum Bacteroidetes may be a microorganism belonging to the family Bacteroidaceae, Prevotellaceae, Rikenellaceae, or Porphyromonadaceae. The microorganism belonging to the phylum Bacteroidetes may be a microorganism belonging to the genus *Bacteroides, Xylanibacter, Alistipes*, or *Parabacteroides*. The microorganism belonging to the phylum Bacteroidetes may be a microorganism belonging to the species *B. fragilis, B. melaninogenicus, B. oralis, B. vulgatus, B. acidifaciens, B. thetaiotaomicron, B. caccae, B. stercoris, B. coprocola, B. eggerthii, B. intestinalis, B. massiliensis, B. ovatus, B. plebeius, B. uniformis, B. galacturonicus, B. merdae, B. capillosus, P. intermedia, P. aurantiaca, P. copri, P. nigrescens, P, brevis, P. denticola, P. heparinolytica, P. paludivivens, P, ruminicola, X. oryzae, A, finegoldii, A. indistinctus. A, putredinis, A. onderdonkii*, or *P. Merdae*, but the present disclosure is not limited thereto. The microorganism belonging to the phylum Finnicutes may be a microorganism belonging to the family Lactobacillaceae, Ruminococcaceae, Lachnospiraceae, Leuconostocaceae, Peptostreptococcaceae, Veillonellaceae, Clostridiaceae, Enterococcaceae, Streptococcaceae, Staphylococcaceae, Eubacteriaceae, Bacillaceae, or Butyrate-producing bacterium. The microorganism belonging to the phylum Firmicutes may be a microorganism belonging to the genus *Pediococcus, Lactobacillus, Ruminococcus, Subdoligranulum, Roseburia. Acetitomaculum, Coprococcus, Leuconostoc, Weissella, Peptostreptococcus, Veillonella, Faecalibacterium, Clostridium, Dorea, Anaerotruncus, Enterococcus, Streptococcus, Lactococcus, Staphylococcus, Anaerofustis, Eubacterium, Bacillus*, or Butyrate-producing bacterium. The microorganism belonging to the phylum Firmicutes may be a microorganism belonging to the species *P. acidolactis, P. pentosaceus, L. plantarum, L. acidophilus, L. Paracasei, L. reuteri, L. helveticus, L. rhamnosus, L. Bulgaricus, L. casei, L. fermentum, L. gasseri, L. helveticus, L. johnsonii, L, salivarius, R, obeum, R. gnavus, R. torques, R. bromii, R. lactaris, Subdoligranulum sp. DJF VR33k2, S. variabile, R. intestinalis, R. hominis, A. ruminis, C. eutactus, C. comes, L. mesenteroides, L. carnosum, L. citreum, L. gasicomitatum, L. gellidum, L. inhae, L. kimchii, L. lactis, L. mesenteroides* subsp. *mesenteroides, L. paramesenteroides, W. cibaria, W. confusa, W. koreensis, W. soli, W. viridescens, P. anaerobius, V. parvula, F. prausnitzii, C. perfringens, C. difficile, C. botulinum, C. tetani, C. septicum, C. asparagiforme, C. butyricum, C. bolteae, C. leptum, C. orbiscindens, C. saccharolyticum, C. scindens, C. asparagiforme, C. nexile, D. longicatena, D. formicigenerans, A. colihominis, E. faecalis, E. faecium, S. thermophilus, S. pyogenes, S. faecium, S. faecalis, L. lactis, S. aureus, A. stercorihominis, E. tenue, E. ventriosum, E. rectale, E. eligens, E. siraeurn, E. hallii, B. cereus, B. subtilis, B. coagulans, B. mesentericus, B. licheniformis, B. polyfermenticus*, Butyrate-producing bacterium A1-86, Butyrate-producing bacterium A2-207, Butyrate-producing bacterium M21/2, Butyrate-producing bacterium SL6/1/1, Butyrate-producing bacterium SSC/2, or Butyrate-producing bacterium T1-815, but the present disclosure is not limited thereto. The microorganism belonging to the phylum Actinobacteria may be a microorganism belonging to the family Bifidobacteriaceae, Mycobacteriaceae, or Propionibacteriaceae. The microorganism belonging to the phylum Actinobacteria may be a microorganism belonging to the genus *Bifidobacterium, Mycobacterium*, or *Propionibacterium*. The microorganism belonging to the phylum Actinobacteria may be a microorganism belonging to the species *B. breve, B. bifidurn, B. longum, B. infantis, B. pseudolongurn, B. lactis, B. animalis, B. adolescentis, B. pseudocatenulatum, B. puliorum, B. ruminantium, B. sirniae, B. thermophilum, M. avium* spp. *paratuberculosis*, or *P. acnes*, but the present disclosure is not limited thereto. The microorganism belonging to the phylum Proteobacteria may be a microorganism belonging to the family Enterobacteriaceae, Helicobacteraceae, Desulfovibrionaceae, Alcaligenaceae, Vibrionaceae, Pseudomonadaceae, or Campylobacteraceae. The microorganism belonging to the phylum Proteobacteria may be a microorganism belonging to the genus *Salmonella, Klebsiella, Enterobacter, Shigella, Escherichia, Yersinia, Proteus, Edwardsiella, helicobacter, Desulfovibrio, Bordetella, Vibrio, Pseudomonas*, or *Campylobacter*. The microorganism belonging to the phylum Proteobacteria may be a microorganism belonging to the species *S. enterica* subsp. *Enterica serovar, S. typhimurium, S. enteritidis, K. pneumoniae, K. oxytoca, E. cloacae, E. aerogenes, S. flexneri, S. dysenteriae, S. boydii, S. sonni, E. coli, E. coli* O157, *Y. enterocolitica, Y. pestis, Y. pseudotuberculosis, P. mirabilis, E. tarda, H. hepaticus, H. pylori, D. desulfuricans, B. pertussis, V. cholerae, V. parahemolyticus, V. vulnificus, P. aeruginosa*, or *C. jejuni*, but the present disclosure is not limited thereto. The microorganism belonging to the phylum Verrucomicrobia may be a microorganism belonging to the family Verrucomicrobiaceae. The microorganism belonging to the phylum Verrucomicrobia may be a microorganism belonging to the genus *Akkermansia*. The microorganism belonging to the phylum Verrucomicrobia may be a microorganism belonging to the species *A. Muciniphila*, but the present disclosure is not limited thereto. The microorganism belonging to the phylum Fusobacteria may be a microorganism belonging to the family Fusobacteriaceae. The microorganism belonging to the phylum Fusobacteria may be a microorganism belonging to the genus *Fusobacterium*. The microorganism belonging to the phylum Fusobacteria may be a microorganism belonging to the species *F. nucleatum, F. mortiferum*, or *F. necrophorum*, but the present disclosure is not limited thereto.

The second drainage control unit 290 may be installed in each of the accommodation units 240 and able to control the storage or discharge of the fecal sample accommodated in each of the accommodation units 240. The discharge pipe 250 may be connected to each of the plurality of accommodation units 240, and a plurality of discharge pipes 250 may be connected to a single confluent pipe 260. The discharge pipe 250 may include a plurality of discharge pipes 250 to correspond to the plurality of accommodation units 240. Referring to FIG. 2, for example, the discharge pipe 250 may include first, second, third, fourth, fifth, and sixth discharge pipes 251, 252, 253, 254, 255, and 256 to correspond to the six accommodation units 240. One end of the first discharge pipe 251 is connected to the confluent pipe 260, and another end thereof is connected to the first accommodation unit 241. One end of the second discharge pipe 252 is connected to the confluent pipe 260, and another end thereof is connected to the second accommodation unit 242. One end of the third discharge pipe 253 is connected to the confluent pipe 260, and another end thereof is connected to the third accommodation unit 243. One end of the fourth discharge pipe 254 is connected to the confluent pipe 260, and another end thereof is connected to the fourth accommodation unit 244. One end of the fifth discharge pipe 255 is connected to the confluent pipe 260, and another end thereof is connected to the fifth accommodation unit 245. One end of the sixth discharge pipe 256 is connected to the confluent pipe 260, and another end thereof is connected to the sixth accommodation unit 246. In addition, under control of the second drainage control units 290, the fecal sample accommodated in each of the plurality of accommodated units 240 may be transferred to the confluent pipe 260 via the plurality of discharge pipes 250. The second drainage control units 290 may control the fecal sample to be accommodated and stored in the respective multiple accommodation units 240, and may also control, until the sensor unit 300 detects a microorganism in the fecal sample accommodated in each of the plurality of accommodation units 240, the fecal sample not to be discharged via the discharge pipe 250 or the fecal sample to be discharged so that the fecal sample having a detected microorganism therein is discharged via the discharge pipe 250. In addition, the confluent pipe 260 may be connected to the inside of a toilet 20 so that the fecal sample can be discharged into the toilet 20 via the confluent pipe 260, but the present disclosure is not limited thereto.

The sensor unit 300 may include a wave source 310 and a detection unit 320. The sensor unit 300 may be provided on the accommodation unit 240 between the sub-pipe 230 and the discharge pipe 250. The sensor unit 300 may detect a microorganism in the fecal sample accommodated in the accommodation unit 240 by using waves. In this regard, the waves may be visible light, light suitable for a luminescent or fluorescent material, ultraviolet light, infrared light, or electronic light, but the present disclosure is not limited thereto. The sensor unit 300 may detect a microorganism in the fecal sample accommodated in the accommodation unit 240 by using waves, thereby generating first information.

The wave source 310 may emit waves towards the fecal sample accommodated in each of the accommodation units 240. As the wave source 310, any type of source device capable of generating waves may be applied, and the wave source 310 may be a laser capable of emitting coherent light, for example, light of a specific wavelength band. The wave source 310 may emit visible light, light suitable for a luminescent or fluorescent material, ultraviolet light, infrared light, electronic light, or a combination thereof, but the present disclosure is not limited thereto. The emission may be performed at least once at a pre-set time point. That is, the emission may generate at least first waves, and may generate first waves and second waves. Meanwhile, the first waves and the second waves are merely one example selected for convenience of explanation, and the emission may generate a greater number of a plurality of waves than the first waves and the second waves.

The detection unit 320 may detect, at a pre-set time point, a signal generated by reflection, refraction, diffraction, scattering, dispersion, or interference of the emitted waves in the fecal sample. In this regard, the time point refers to a moment in a continuous flow of time, and time points may be previously set at the same time interval, but the present disclosure is not limited thereto, and time points may also be previously set at arbitrary time intervals. That is, the time point may be at least previously set as a first time point after an arbitrary time interval elapses after the fecal sample is accommodated in the accommodation unit 240. The detection unit 320 may include a detection member corresponding to the type of the wave source 310. For example, when a laser with a visible light wavelength band is used, a CCD camera, which is an image photographing apparatus, may be used, and when a laser with a light wavelength band corresponding to a fluorescent material is used, a fluorescence detector including a CCD camera, which is an image photographing apparatus, may be used.

The detection unit 320 may detect, at a first time point, a signal generated by the emitted waves in the fecal sample, or detect the signal at a first time point and a second time point, and provide the microorganism detection results to a control unit 400. Meanwhile, the first time and the second time are merely one example selected for convenience of explanation, and the detection may be performed at a greater number of a plurality of time points than the first time point and the second time point. Meanwhile, in one embodiment of the present disclosure, for the first waves, only the difference between a detection result at the first time point and a detection result at the second time point is not used, and the difference between a detection result at the first time point and/or a detection result at the second time point for the first waves, and a detection result at the first time point and/or a detection result at the second time point for the second waves may be used. Furthermore, results of detecting, at a plurality of time points, signals generated in the fecal sample by a plurality of waves emitted at a plurality of time points may be used.

The signal generated in the fecal sample by the emitted waves is represented by the pattern and/or intensity of the signal. The detection results become first information. When a microorganism is present in the fecal sample, the emitted waves may provide different signals at a plurality of time points due to the amount of microorganism in the fecal sample and the movement of the microorganism.

The control unit 400 may acquire the results of detecting, by the sensor unit 300, a microorganism in the fecal sample accommodated in each accommodation unit, i.e., the first information generated by detecting a microorganism, and may estimate, on the basis of the first information, the type of a target microorganism in a set environment and the concentration thereof. The detection unit 320 may rapidly detect a microorganism in the fecal sample, and the control unit 400 may estimate in real time the type of target microorganism and the concentration thereof. Pieces of information about the estimated type of target microorganism and the estimated concentration thereof may be compared and analyzed between the plurality of accommodation units 240. In addition, the pieces of information about the estimated type of target microorganism and the estimated concentration thereof may be compared and analyzed at a plurality of time points, for example, 1-minute intervals, 2-minute intervals, 3-minute intervals, 5-minute intervals, 10-minute intervals, 20-minute intervals, 30-minute intervals, 1-hour intervals, 3-hour intervals, 6-hour intervals, 1-day intervals, 1-week intervals, 1-month intervals, 1-year intervals, or a longer consecutive time point. In addition, the pieces of information about the estimated type of target microorganism and the estimated concentration thereof may be compared and analyzed between individuals. On the basis of the comparison and analysis results, information about the intestinal environment or health condition of a user may be provided.

FIG. 4 is an exemplary view of an intestinal microorganism detection system according to an embodiment of the present disclosure that is realized as a bidet-like application apparatus. Referring to FIG. 4, a bidet 10 including an intestinal microorganism detection system may include a main body portion 11 mounted on a toilet 20, a seating portion 12 which is connected to the main body portion 10 and configured to allow a person to be seated thereon, and a cover portion 13 which is connected to the main body portion 11 so as to open or close the toilet 20 and rotatably configured on the main body portion 11 at a predetermined angle. In addition, the feces accommodation unit 110 of the feces collection unit 100 may be withdrawn from the main body portion 11 to a predetermined length. For example, when a user is seated on the seating portion 12, one end of the feces accommodation unit 110 may correspond to the anus of the user. Specifically, the feces accommodation unit 110 may be withdrawn from the main body portion 11 to a length sufficient for feces discharged from the anus of a user to be accommodated in the end of the feces accommodation unit 110. In other embodiments, when a user is not seated on the seating portion 12, at least a portion of the region of the feces accommodation unit 110 withdrawn from the main body portion 11 may be inserted back into the main body portion 11. In addition, the control unit 400 may take or insert the feces accommodation unit 110 out of or into the main body portion 11 to a predetermined length in response to a command signal from a user. In other embodiments, the feces accommodation unit 110 may be withdrawn from the main body portion 11 at a predetermined inclination. In this regard, it is preferable that the feces accommodation unit 110 is withdrawn from the main body portion 11 at an inclination sufficient for an end of the feces accommodation unit 110 not to come into contact with water accommodated in the toilet 20 so that only feces discharged from a person is collected.

Figure 5:
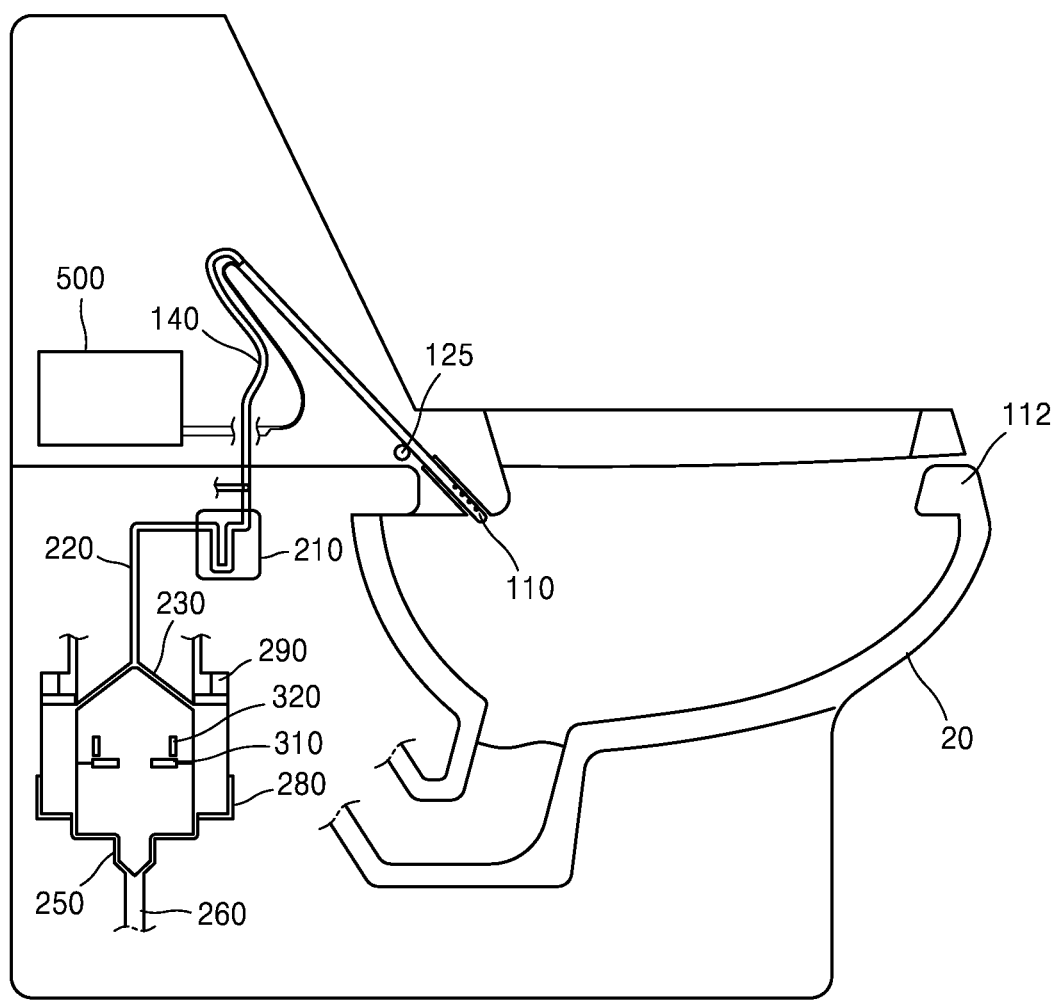
FIG. 5 is an exemplary view of an intestinal microorganism detection system according to an embodiment of the present disclosure that is implemented in an applied apparatus.

Referring to FIGS. 4 and 5, it is illustrated that the feces collection unit 100 is installed in the main body portion 11 of the bidet 10, a portion of the feces accommodation unit 110 of the feces collection unit 100 is withdrawn from the main body portion 11, and at least a portion of the transfer pipe 140 is withdrawn from the main body portion 11 and connected to the storage unit 200 and the sensor unit 300, which are provided outside the main body portion 11, but the present disclosure is not limited thereto. The feces collection unit 100, the storage unit 200, and the sensor unit 300 may also be installed in the main body portion 11.

Figure 6:
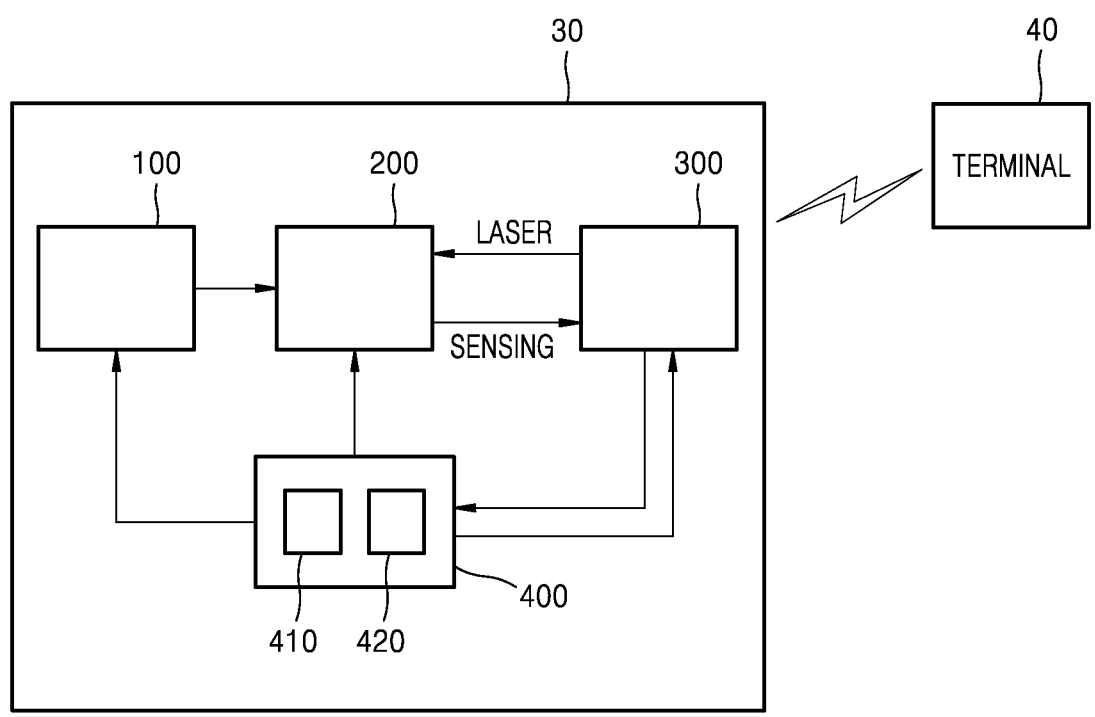
FIG. 6 is a schematic conceptual diagram illustrating an intestinal microorganism detection system according to an embodiment of the present disclosure.

FIG. 6 is a schematic conceptual view of an intestinal microorganism detection system 30 according to an embodiment of the present disclosure. Referring to FIG. 6, the intestinal microorganism detection system 30 according to an embodiment of the present disclosure may include the feces collection unit 100, the storage unit 200, the sensor unit 300, and the control unit 400 for controlling these units.

The feces collection unit 100 may collect feces discharged from an animal including a mammal, for example, a human, mix the collected feces with fluid to thereby generating a fecal sample, and transfer the generated fecal sample to the storage unit 200. The storage unit 200 may temporarily accommodate or store the fecal sample transferred from the feces collection unit 100 for a predetermined period of time and discharge the stored fecal sample after the predetermined period of time. The sensor unit 300 may detect a microorganism in the fecal sample that has been temporarily stored in the storage unit 200 for the predetermined period of time and transmit the detection results to the control unit 400. The control unit 400 may control, when a command signal is input from a user, the operations of the feces collection unit 100 to collect feces and generate a fecal sample by mixing the collected feces with fluid, according to a predetermined order. The control unit 400 may control an operation of transferring the fecal sample generated from the feces collection unit 100 to the storage unit 200, and may control the sensor unit 300 to perform a sensing operation for detecting a microorganism in the fecal sample accommodated in the storage unit 200. In addition, when the sensor unit 300 acquires the results of detecting a microorganism in the fecal sample accommodated in each accommodation unit, i.e., first information, the control unit 400 may estimate, on the basis thereof, the type of target microorganism in a set environment and the concentration thereof. When performing such an operation, the control unit 400 may control and communicate with the feces collection unit 100, the storage unit 200, and the sensor unit 300 via wired and/or wireless communication. In addition, the control unit 400 may include an input device 410 for receiving a command signal from a user, and the user may manipulate the input device 410 to input the command signal to the control unit 400. In this regard, the input device 410 may be a physical button, a touch panel, or a combination thereof. In addition, the control unit 400 may further include an output unit 420 capable of visually and/or acoustically displaying, according to a command signal, information about at least one of: operation processes of the feces collection unit 100, the storage unit 200, and the sensor unit 300; first information; and the estimated type of target microorganism and concentration thereof. The output unit 420 may be a speaker, a display device, or a combination thereof. The display device may include a liquid crystal display (LCD), a thin time transistor-liquid crystal display (TFT LCD), an organic light-emitting diode (OLED), a flexible display, a 3D display, or an e-ink display. As illustrated in FIG. 6, the control unit 400 includes the output unit 420, but the present disclosure is not limited thereto, and the output unit 420 may be configured as a module independently of the control unit 400, and may receive information from the control unit 400 and display the information. In other embodiments, the control unit 400 may also transmit, to a terminal 40, information about at least one of: operation processes of the feces collection unit 100, the storage unit 200, and the sensor unit 300; first information; and the estimated type of target microorganism and concentration thereof, via a wired and/or wireless communication means. In another embodiment, the control unit 400 may transmit, to the terminal 40, the first information acquired by the sensor unit 300, and the terminal 40 may also analyze the received first information. In addition, although not shown in the drawings, the first information may also be provided to a server (not shown). When the information about at least one of first information and the type of target microorganism and concentration thereof is uploaded, the intestinal microorganism detection system 30 registers the information on a server (not shown), and provides other users with an interface capable of searching for data registered on the server (not shown). The intestinal microorganism detection system 30 according to an embodiment may construct, as database, the distribution of intestinal microorganisms and the like through the above-described processes. The terminal 40 may be a personal computer or a portable terminal that is capable of using a web service in a wired/wireless communication environment.

Figure 7:
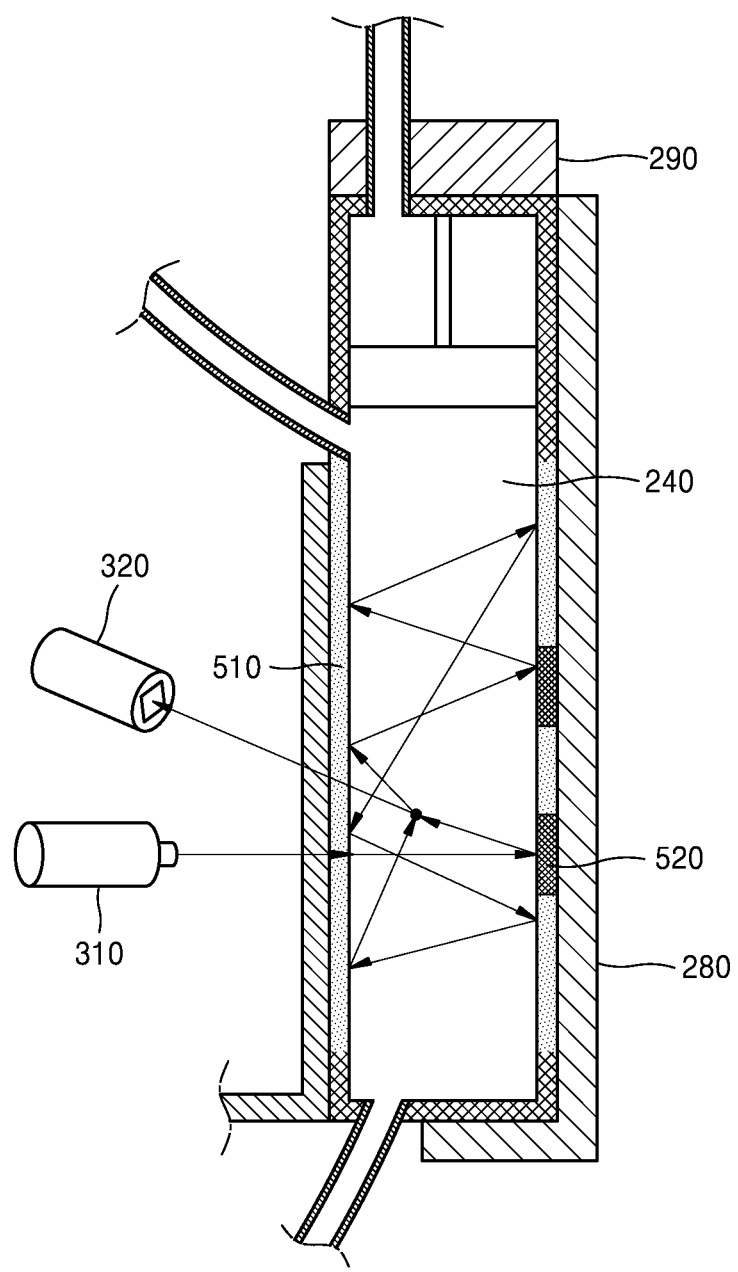
FIG. 7 is a conceptual view for explaining a process of detecting microorganisms using an accommodation unit and a sensor unit.

FIG. 7 is a conceptual view for explaining a process of detecting a microorganism using the accommodation unit 240 and the sensor unit 300. Referring to FIG. 7, the accommodation unit 240 may allow the fecal sample introduced via a sub-pipe to be discharged via a discharge pipe. In addition, the accommodation unit 240 may include a multiple scattering amplification region 510 for amplifying the number of multiple scattering events in the fecal sample of waves that are incident between the sup-pipe and the discharge pipe. In one embodiment, the accommodation unit 240 may store or discharge the fecal sample in a state in which the entire area of a cross-section of the accommodation unit 240 is 100% filled or the inside thereof is completely filled. When the fecal sample is stored, introduced, or discharged in the state in which the cross-section of the accommodation unit 240 is not 100% filled, a wave-front may occur in the fecal sample due to flow of the fecal sample. Such a wave-front may act as a scatterer, and thus may act as noise in detecting a microorganism through the sensor unit 300. Thus, to minimize such noise, the accommodation unit 240 may store, introduce, or discharge the fecal sample in the state in which the entire area of the cross-section of the accommodation unit 240 or the inside thereof is completely filled.

In addition, the multiple scattering amplification region 510 of the accommodation unit 240 may reflect at least some waves emitted from the fecal sample into the fecal sample, thereby being capable of amplifying the number of multiple scattering events in the fecal sample. The multiple scattering amplification region 510 may include a multiple scattering material. For example, the multiple scattering material may include particles having a large refractive index and a diameter of micrometers or less, for example, titanium oxide ($TiO_2$) nanoparticles. In this regard, the multiple scattering amplification region 510 may be formed by coating an outer surface of a main body of the accommodation unit 240 with a multiple scattering material. However, the present disclosure is not limited thereto. In other embodiments, the multiple scattering amplification region 510 may also be formed by including a multiple scattering material in the main body of the accommodation unit 240.

In another embodiment, the multiple scattering amplification region 510 may include a multiple scattering amplification portion (not shown) that is provided adjacent to the main body of the accommodation unit 240 and reflects, into the accommodation unit 240, at least some of the waves emitted to the outside of the accommodation unit 240. In this regard, the multiple scattering amplification portion (not shown) may be configured such that the waves emitted from the accommodation unit 240 move back and forth in a space between the accommodation unit 240 and the multiple scattering amplification portion (not shown) at least six times or more. Meanwhile, the multiple scattering amplification region 510 may be provided in a portion or the entire region between the sub-pipe and the discharge pipe of the accommodation unit 240.

Meanwhile, at least a portion of the multiple scattering amplification region 510 may consist of a reflection region 520 that completely reflects the waves emitted from the fecal sample into the fecal sample. The reflection region 520 may minimize the emission of waves to the outside of the accommodation unit 240 from the fecal sample, thereby increasing a microorganism detection rate of the sensor unit 300. The reflection region 520 may be arranged to face an incidence region into which waves are incident from the wave source 310 of the sensor unit 300. By completely reflecting, into the fecal sample, the waves emitted from the wave source 310, the reflection region 520 may increase the amount of waves that can be multi-scattered in the fecal sample, thereby increasing the microorganism detection rate of the sensor unit 300. In other embodiments, the entire region of the multiple scattering amplification region 510, except for a movement path of waves emitted to the detection unit 320 of the sensor unit 300 may also consist of a reflection region.

Thus, the waves in the accommodation unit 240 may fill at least 10%, at least 20%, at least 30%, at least 40%, at least 50%, at least 60%, at least 70%, at least 80%, at least 90%, or 100% of the entire area of the cross-section of the accommodation unit 240.

The multiple scattering amplification regions 510 of the accommodation unit 240 may be sequentially arranged in a longitudinal direction between the sub-pipe and the discharge pipe and include a plurality of divided regions D1, D2, and D3 (not shown) having different scattering rates. In this regard, the intestinal microorganism detection system 30 may include a plurality of sensor units 300 arranged to correspond to the plurality of divided regions D1, D2, and D3 (not shown). The plurality of divided regions D1, D2, and D3 (not shown) may be spaced apart from each other at constant intervals, but the present disclosure is not limited thereto. In other embodiments, the plurality of divided regions D1, D2, and D3 (not shown) may be connected to each other. In addition, the plurality of divided regions D1, D2, and D3 (not shown) may have scattering rates that are constantly increased or decreased in the longitudinal direction of the accommodation unit 240. In this regard, the plurality of divided regions D1, D2, and D3 (not shown) may include different scattering materials, or may have different scattering rates by varying the degree to which a scattering material is included therein.

In one embodiment, when the multiple scattering amplification region 510 includes a first divided region D1 (not shown), a second divided region D2 (not shown), and a third divided region D3 (not shown), the intestinal microorganism detection system 30 may include a first sensor unit 300-1 (not shown), a second sensor unit 300-2 (not shown), and a third sensor unit (300-3) (not shown) to correspond to the divided regions. The first sensor unit 300-1 (not shown), the second sensor unit 300-2 (not shown), and the third sensor unit (300-3) (not shown) may have different microorganism detection rates in correspondence with the scattering rates of the first divided region D1 (not shown), the second divided region D2 (not shown), and the third divided region D3 (not shown). The intestinal microorganism detection system 30 may precisely and accurately detect a microorganism through several detections by varying sensitivity on a path through which fluid moves.

Figure 8:
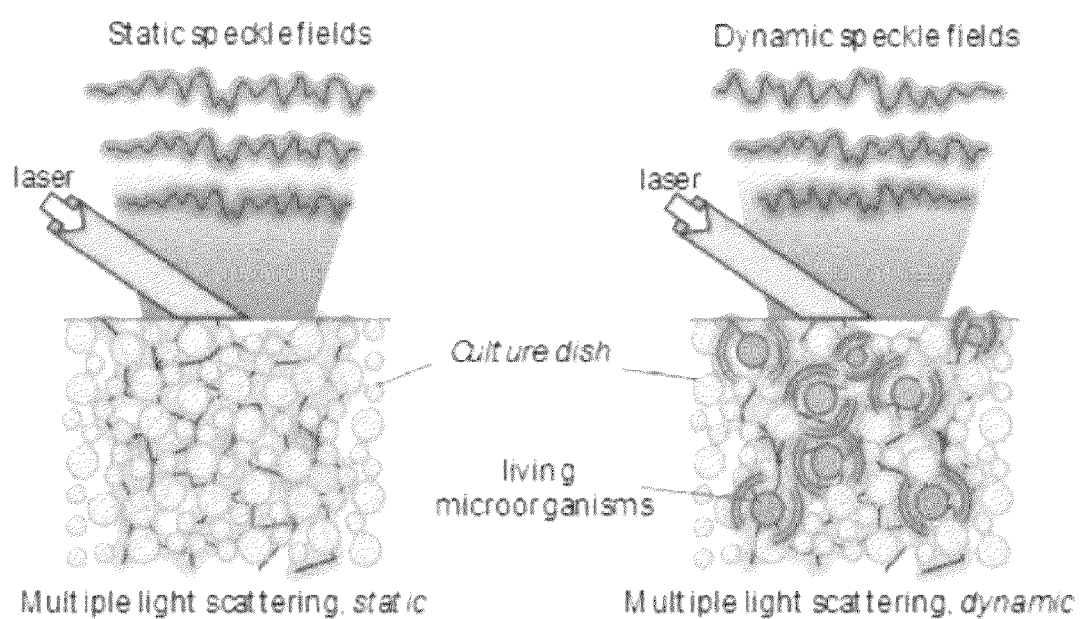
FIG. 8 is a view for explaining a principle of a chaotic wave sensor according to an embodiment of the present disclosure.

Meanwhile, the sensor unit 300 may be provided on the accommodation unit 240 between the sub-pipe and the discharge pipe. In one embodiment, the sensor unit 300 may be a chaotic wave sensor. The principle of the chaotic wave sensor of the present disclosure will now be described with reference to FIG. 8. FIG. 8 is a view for explaining the principle of a chaotic wave sensor according to an embodiment of the present disclosure.

In the case of a material having a homogeneous internal refractive index, such as glass, refraction occurs in a certain direction when light is irradiated. However, when a material having a heterogeneous internal refractive index is irradiated with coherent light such as laser beams, very complex multiple scattering occurs inside the material.

Referring to FIG. 8, in light or waves (hereinafter, referred to as waves for simplicity) emitted from a wave source, some of the waves that have been scattered through complicated paths due to multiple scattering pass through a test target surface. Waves passing through multiple points in the test target surface generate constructive interference or destructive interference, and the constructive/destructive interference of the waves generates grain patterns (speckles). In the present specification, the waves scattered in the complicated paths are referred to as "chaotic waves," and the chaotic waves may be detected through wave speckles. The wave speckles refer to a grain-shaped pattern generated by the constructive/destructive interference of waves. The waves may be coherent waves, for example, laser beams or holograms.

The left side of FIG. 8 shows a state in which a stable medium is irradiated with coherent light. When a stable medium, in which an internal component does not move, is irradiated with coherent light (e.g., laser beams), a stable speckle pattern without a variation may be observed. However, as shown in the right side of FIG. 8, when an unstable medium having an internal component that is moving, such as microorganism, is included therein, the speckle pattern varies.

That is, due to the fine activity of life (e.g., movement in cells, movement of microorganism, and movement of mites) of living microorganisms, an optical path may be finely changed over time. Since the speckle pattern is generated by interference of the waves, a fine change in the optical path may cause variation in the speckle pattern. Accordingly, when a temporal variation in the speckle pattern is measured, the activities of living microorganisms may be rapidly measured. As such, when the variation in the speckle pattern over time is measured, the presence or absence of living organisms and concentration thereof may be identified, and furthermore, types of living organisms may also be identified.

In the present specification, a structure for measuring the variation in the speckle pattern is defined as a chaotic wave sensor.

Meanwhile, since a fluid such as water does not contain a heterogeneous material that generates scattering inside as described above, when microorganisms are not present, a variation in the wave speckle pattern over time cannot be generated. In contrast, the intestinal microorganism detection system 30 according to an embodiment of the present disclosure may multi-scatter waves through the multiple scattering amplification region 510 of the accommodation unit 240, which has already been described, thereby generating a stable wave speckle pattern. In the intestinal microorganism detection system 30, in the case where a microorganism is present in the fecal sample stored in the accommodation unit 240, a path of the waves may be finely changed by movement of the microorganism. The fine change in the path of the waves may generate a change in the speckle pattern, and accordingly, by measuring a temporal change in the speckle pattern, the presence or absence of a microorganism in the fecal sample and the amount thereof may be rapidly detected.

In one embodiment, to form speckles in the fecal sample, a laser having good coherence may be used as a wave source. In this regard, the shorter the spectral bandwidth of the wave source that determines coherence of the laser wave source, the greater the measurement accuracy. That is, when a coherence length increases, the measurement accuracy may increase. Accordingly, a laser having a spectral bandwidth that is less than a predetermined reference bandwidth may be used as the wave source 310, and when the spectral bandwidth is less than the reference bandwidth, the measurement accuracy may increase. For example, the spectral bandwidth of the wave source may be set to satisfy the following condition of Equation 1 below.

$$\text{Spectral bandwidth} < 1 \text{ nm} \qquad \text{[Equation 1]}$$

According to Equation 1, when light is irradiated into the fecal sample at every reference time in order to measure a variation in the pattern of the wave speckle, the spectral bandwidth of the wave source 310 may be maintained to be less than 1 nm.

The detection unit 320 may detect the wave speckle that is generated by multiple scattering of the irradiated waves in the fecal sample at every pre-set time point. The detection unit 320 may detect the wave speckle at least at a first time point, detect wave speckles at a first time point and a second time point, and provide the wave speckles for the control unit 400. Meanwhile, the first time and the second time are merely one example selected for convenience of explanation, and the detection unit 320 may detect wave speckles at a greater number of a plurality of time points than the first time point and the second time point.

Specifically, when the fecal sample is irradiated with waves, the incident waves may form a wave speckle by multiple scattering. Since wave speckles occur due to light interference, when no microorganism is present in the fecal sample, a constant interference pattern may always be formed over time by the multiple scattering amplification region. In contrast, when a microorganism is present in the fecal sample, wave speckles may be changed over time by the amount of microorganism and movement of the microorganism. Furthermore, the survival or proliferative rates of a target microorganism in the fecal sample and microorganisms other than the target microorganism are differently controlled, and thus wave speckles may be changed over time by the amount of microorganism and movement of the microorganism.

Alternatively, when the fecal sample is irradiated with first waves and irradiated with second waves at another time point, the incident first waves may form a first wave speckle by multiple scattering, and the second waves may form a second wave speckle by multiple scattering. Since the survival or proliferative rates of a target microorganism in the fecal sample and microorganisms other than the target microorganism are differently controlled, the first wave speckle and the second wave speckle may be changed over time by the amount of microorganism and the movement of the microorganism. The detection unit 320 may detect, at every predetermined time point, these wave speckles that vary over time and provide the results for the control unit 400.

The detection unit 320 may detect wave speckles, i.e., the first wave speckle and/or the second wave speckle, at a rate sufficient to detect the movement of a microorganism, for example, at a rate of about 25 frames/second to about 30 frames/second.

Meanwhile, when an image sensor is used as the detection unit 320, the image sensor may be arranged such that a size d of one pixel of the image sensor is smaller than or the same as the grain size of the speckle pattern. For example, to satisfy the condition of Equation 2 below, the image sensor may be arranged in an optical system included in the detection unit 320.

$$d \leq \text{speckle grain size} \qquad \text{[Equation 2]}$$

As shown in Equation 2, the size d of one pixel in the image sensor has to be equal to or less than the grain size of the speckle pattern, but when the size of the pixel is too small, undersampling occurs, and thus it may be difficult to use pixel resolution. Accordingly, to achieve an effective signal to noise ratio (SNR), the image sensor may be arranged such that a maximum of five pixels or less are positioned to correspond to the speckle grain size.

The control unit 400 may acquire, by using the detected first wave speckle, a temporal correlation of the detected first wave speckle. Alternatively, the control unit 400 may acquire, by using the detected first wave speckle, the temporal correlation of the detected first wave speckle, and acquire, by using the detected second wave speckle, a temporal correlation of the detected second wave speckle. Alternatively, the control unit 400 may acquire, by using the detected first wave speckle and the detected second wave speckle, a temporal correlation between the detected first wave speckle and the detected second wave speckle. The control unit 400 may estimate in real time, on the basis of the acquired temporal correlation, at least one selected from the presence or absence of a microorganism in the fecal sample, the type of microorganism, and the concentration of the microorganism. In the present specification, real-time means that a series of processes of feces collection, accommodation of the fecal sample, microorganism detection, and estimation of the type and concentration of microorganism are continuously processed without interruption. Thus, the real-time estimation of the at least one selected from the presence or absence of a microorganism in the fecal sample, the type of microorganism, and the concentration of the microorganism may be performed within about 1 day, about 24 hours, about 20 hours, about 12 hours, about 10 hours, about 8 hours, about 6 hours, about 5 hours, about 4 hours, about 3 hours, about 2 hours, about 1 hour, about 30 minutes, about 20 minutes, about 10 minutes, about 5 minutes, about 3 minutes, about 2 minutes, or about 1 minute.

In one embodiment, the control unit 400 may estimate at least one selected from the presence or absence of a microorganism, the type of microorganism, and the concentration of the microorganism by using a difference between first image information of a first wave speckle detected at a first time point and second image information of a first wave speckle detected at a second time point different from the first time point. In this regard, the first image information and the second image information may be at least any one of pattern information of the first wave speckle and intensity information of the waves. Meanwhile, in one embodiment of the present disclosure, only the difference between the first image information at the first time point and the second image information at the second time point is not used, and furthermore, image information of a plurality of first wave speckles at a plurality of time points may be used. The control unit 400 may calculate a temporal correlation coefficient between images by using image information of first wave speckles generated at a plurality of predetermined time points, and may estimate, on the basis of the temporal correlation coefficient, at least one selected from the presence or absence of a microorganism in the fecal sample, the type of microorganism, and the concentration of the microorganism. The temporal correlation between images of the detected first wave speckles may be calculated using Equation 3 below.

$$\overline{C}(x, y; \tau) = \frac{1}{T-\tau}\sum_{t=1}^{T-\tau} \tilde{I}(x, y; t)\tilde{I}(x, y; t+\tau)\delta t \qquad \text{[Equation 3]}$$

In Equation 3, $\overline{C}$ denotes a temporal correlation coefficient, $\tilde{I}$ denotes standardized light intensity, (x,y) denotes a pixel coordinate of a camera, t denotes a measurement time, T denotes a total measurement time, and $\tau$ denotes a time lag. According to Equation 3, the temporal correlation coefficient may be calculated, and as one embodiment, by analyzing whether the temporal correlation coefficient is below or greater than a predetermined reference value, at least one selected from the presence or absence of a microorganism, the type of microorganism, and the concentration of the microorganism may be estimated. Specifically, when the temporal correlation coefficient is beyond a predetermined error range and below or greater than the reference value, it may be estimated that the concentration of the microorganism increases or decreases.

In one embodiment, the control unit 400 may estimate at least one selected from the presence or absence of a microorganism, the type of microorganism, and the concentration of the microorganism by using a difference between first image information of a first wave speckle detected at time point 1 and/or second image information of a first wave speckle detected at time point 2 different from the first time point, and first image information of a second wave speckle detected at time point 1' and/or second image information of a second wave speckle detected at time point 2' different from the time point 1'. In this regard, the first image information and the second image information of the first wave speckle and the second wave speckle may be at least any one of pattern information of the first wave speckle and the second wave speckle and intensity information of the waves. Meanwhile, in one embodiment of the present disclosure, only the difference between the first image information of a first wave speckle at a first time point and the first image information of a second wave speckle at time point 1' is not used, and furthermore, image information of first wave speckles and second wave speckles at a plurality of time points may be used. A temporal correlation between images of the detected first wave speckle and the detected second wave speckle may be calculated using Equation 3 above.

Figure 9A:
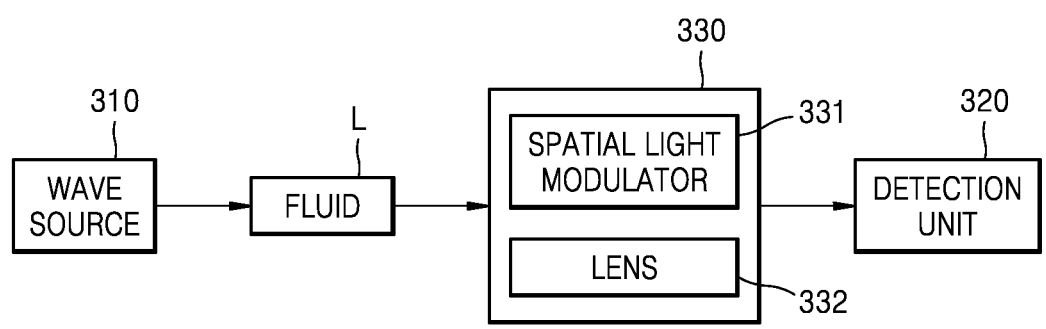
FIGS. 9A and 9B are schematic conceptual views illustrating a sensor unit according to another embodiment of the present disclosure.
Figure 9B:
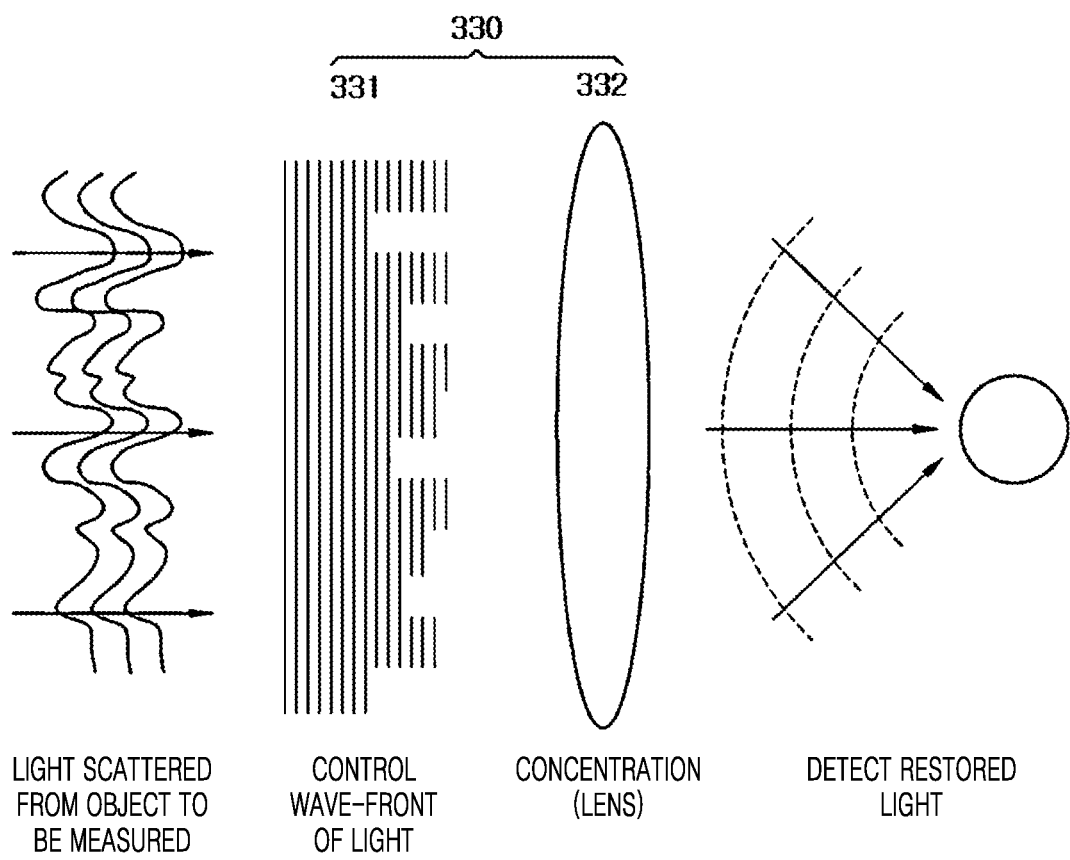

Meanwhile, FIGS. 9A and 9B are schematic conceptual views of the sensor unit 300 according to another embodiment of the present disclosure. Referring to FIGS. 9A and 9B, the sensor unit 300 may further include an optical unit 330 that modulates a first wave signal scattered from the fecal sample into a second wave signal before first waves of the wave source 310 are scattered by the fecal sample. In this regard, the optical unit 330 may include a spatial light modulator (SLM) 331. When waves scattered from an object to be measured are incident, the optical unit 330 may control the wave-front of the scattered waves, restore waves (light) before being scattered, and provide the waves to the detection unit 320. The spatial light modulator 331 may allow waves (light) scattered from the sample to be incident thereon. The spatial light modulator 331 may control the wave-front of the waves scattered from the sample to be provided to a lens 332. The lens 332 may concentrate the controlled light and provide the concentrated light back to the detection unit 320. The detection unit 320 may detect waves concentrated on the lens, restore the detected waves into waves initially emitted from a wave source before being scattered, and emit the restored waves. In this regard, when a microorganism is not present in a stable medium, i.e., fluid, the optical unit 330 may restore, into waves before being scattered, a first wave signal scattered from the fluid. However, when a microorganism is present in the fluid, the first wave signal is changed by the movement of the microorganism, which makes it difficult to detect a phase-controlled wave-front, and thus, it is impossible to modulate the first wave signal into a second wave signal having a phase-conjugated wave-front. The sensor unit 300 including the optical unit 330, which has been described above, may more finely estimate the presence or absence of a microorganism by using such a difference in the second wave signal.

The sensor unit 300 may further include a wave path changing unit (not shown) through which waves may be irradiated into the plurality of accommodation units 240. The wave path changing unit (not shown) may be made of a micromirror. The wave path changing unit (not shown) may be provided with a reflective surface to reflect incident waves towards the plurality of accommodation units 240. The wave path changing unit (not shown) may be finely driven by a driving control unit (not shown). In another embodiment, the wave path changing unit (not shown) is finely driven by the control unit 400, and accordingly, waves may be irradiated to each of the plurality of accommodation units 240. For the micromirror constituting the wave path changing unit (not shown), various configurations, in which mechanical displacement of the reflective surface can occur in accordance with electrical control, may be employed. For example, as the wave path changing unit (not shown), a generally known micro electromechanical system (MEMS) mirror, a digital micromirror device (DMD), or the like may be employed.

The sensor unit 300 may include, instead of the above-described wave path changing unit (not shown), a driving means (not shown) that is connected to the wave source 310 and the detection unit 320 and moves the position of each thereof. While the wave source 310 and the detection unit 320 are moved to a position corresponding to that of each of the plurality of accommodation units 240 via the driving means (not shown), the presence or absence of a microorganism in fluid accommodated in each of the plurality of accommodation units 240 may be detected.

Hereinafter, a method of determining, in the control unit 400, the type of microorganism and the concentration thereof by using a wave speckle will be described in detail.

The plurality of accommodation units 240 are respectively exposed to different environments by the environment control units 280, and thus it is possible to differently control the survival or proliferative rate of a target microorganism and the survival or proliferative rates of microorganisms other than the target microorganism, and accordingly, different target microorganisms may survive or proliferate in the plurality of accommodation units 240, respectively, or may die. That is, depending on the type of target microorganism to be detected in each of the accommodation units 240, the environment control units 280 may differently create environmental conditions of the accommodation units 240. By detecting the movement of a living microorganism in each of the plurality of accommodation units 240, it is possible to estimate the concentration of the target microorganism.

The control unit 400 may calculate, for images of wave speckles measured every reference time, a standard deviation of the light intensity of the wave speckles. As microorganisms contained in fluid continuously move, constructive interference and destructive interference may be changed in correspondence with the movements. In this regard, as the constructive interference and the destructive interference are changed, the degree of light intensity may be greatly changed. Then, the control unit 400 may obtain a standard deviation that represents the degree of a change in light intensity and estimate the concentration of microorganisms in the plurality of accommodation units 240. For example, the control unit 400 may compose images of wave speckles measured every predetermined time, and may calculate a standard deviation of the light intensity over time of a wave speckle, i.e., a first wave speckle and/or a second wave speckle, in the composed image. The standard deviation of the light intensity over time of the wave speckle may be calculated based on Equation 4 below.

$$S(x, y) = \sqrt{\frac{1}{T}\sum_{t=1}^{T}(I_t(x, y) - \bar{I})^2} \quad \text{[Equation 4]}$$

In Equation 4, S denotes the standard deviation, (x,y) denotes a pixel coordinate of a camera, T denotes a total measurement time, t denotes a measurement time. It denotes light intensity measured at a time t, and $\bar{I}$ denotes average light intensity over time.

Since constructive and destructive interference patterns vary depending on the movement of a microorganism and a standard deviation value calculated according to Equation 4 increases, the concentration of the microorganism may be measured on the basis thereof. However, a method of measuring the concentration of microorganism is not limited by Equation 4 above, and the concentration of microorganism may be measured according to any method using a difference in the detected wave speckle.

In addition, the control unit 400 may estimate the distribution, i.e., concentration of microorganism contained in the fluid, on the basis of a linear relationship between the size of the standard deviation of the light intensity of the wave speckle and the concentration of microorganism.

As is apparent from the foregoing description, an intestinal microorganism detection system according to embodiments of the present disclosure may rapidly provide information about the presence or absence of an intestinal microorganism, or the intestinal environment or health condition of a user at low cost.

Exemplary embodiments of the present disclosure have been described. It will be understood by those of ordinary skill in the art to which the present disclosure pertains that the present disclosure may be embodied in various modified forms without departing from the essential characteristics thereof. Thus, the embodiments set forth herein should be considered in an illustrative sense only and not for the purpose of limitation. The scope of the present disclosure should be defined by the appended claims rather than the foregoing description, and all differences within the range equivalent thereto should be construed as falling within the scope of the present disclosure.

The invention claimed is:

1. Intestinal microorganism detection system comprising:
a feces collection unit configured to collect the feces of a user;
a storage unit comprising a plurality of accommodation units configured to accommodate a fecal sample, the fecal sample being formed by mixing the feces collected by the feces collection unit with fluid;
a sensor unit configured to detect a microorganism in the fecal sample accommodated in each of the plurality of accommodation units and generate first information, wherein the sensor unit comprises: a wave source configured to emit waves towards the fecal sample accommodated in each accommodation unit; and at least one detection unit configured to detect, every predetermined time point, a wave speckle generated by multiple scattering of the emitted waves in each accommodation unit, and a control unit is configured to acquire a temporal correlation of the detected wave speckle by using the detected wave speckle, and estimates, on the basis of the acquired temporal correlation, the type of intestinal microorganism present in the fecal sample accommodated in each of the plurality of accommodation units and a concentration thereof; and
the control unit configured to estimate, on the basis of the generated first information, the type of intestinal microorganism present in the user and a concentration thereof, wherein the plurality of accommodation units are respectively exposed to different environmental conditions.

2. The Intestinal microorganism detection system of claim 1, wherein the different environmental conditions are conditions in which it is possible to distinguish a predetermined target microorganism and microorganisms other than the target microorganism.

3. The Intestinal microorganism detection system of claim 1, wherein the different environmental conditions are conditions for surviving or proliferating predetermined different target microorganisms.

4. The Intestinal microorganism detection system of claim 1, wherein the environmental condition comprises a pH condition, a carbon dioxide concentration condition, an oxygen concentration condition, an alcohol concentration condition, a temperature condition, a humidify condition, an antibiotic condition, a microorganism-specific marker condition, or a combination thereof.

5. The Intestinal microorganism detection system of claim 1,
wherein each of the plurality of accommodation units accommodates the fecal sample that is distributed in certain amounts.

6. The Intestinal microorganism detection system of claim 1,
wherein the feces collection unit comprises:
a feces accommodation unit configured to accommodate the feces of a user;
a transfer pipe that connects the feces accommodation unit to the storage unit; and
a fluid supply unit configured to supply the fluid to the transfer pipe.

7. The Intestinal microorganism detection system of claim 6, wherein the feces collection unit further comprises a weight measurement sensor, a moisture content measurement sensor, an occult blood measurement sensor, or a combination thereof.

8. The Intestinal microorganism detection system of claim 1, wherein the storage unit comprises:
a main pipe connected to the transfer pipe;
a plurality of sub-pipes that connect the main pipe to each of the plurality of accommodation units;
an environment control unit configured to control an environmental condition of each of the plurality of accommodation units; and
a drainage control unit configured to control discharge of the fecal sample accommodated in each of the plurality of accommodation units.

9. The Intestinal microorganism detection system of claim 8, wherein the storage unit further comprises a filter unit provided in the main pipe, and configured to filter substances of certain sizes or larger in the fecal sample and transfer the filtrate to the sub-pipes.

10. The Intestinal microorganism detection system of claim 1, wherein the sensor unit detects the presence of a microorganism in the fecal sample accommodated in each accommodation unit by using waves.

11. The Intestinal microorganism detection system of claim 1, wherein the sensor unit comprises:
a wave source configured to emit waves towards the fecal sample accommodated in each accommodation unit; and
a detection unit configured to detect, at a predetermined time point, a signal generated by reflection, refraction, diffraction, scattering, dispersion, or interference of the emitted waves in the fecal sample.

12. The Intestinal microorganism detection system of claim 1, wherein each of the plurality of accommodation units comprises a multiple scattering amplification region for amplifying the number of multiple scattering events in each accommodation unit of waves, the waves being incident onto each accommodation unit.

13. The Intestinal microorganism detection system of claim 12, wherein at least a portion of the multiple scattering amplification region reflects, into the fecal sample, at least some of the waves emitted from the fecal sample to thereby amplify the number of multiple scattering events in the fecal sample.

14. The Intestinal microorganism detection system of claim 12, wherein at least a portion of the multiple scattering amplification region comprises a reflection region that reflects, into the fecal sample, at least some of the waves emitted from the fecal sample.

15. The Intestinal microorganism detection system of claim 1, wherein the estimation comprises estimating in real time, on the basis of the acquired temporal correlation, the type of intestinal microorganism present in the fecal sample accommodated in each of the plurality of accommodation units and a concentration thereof.

16. The Intestinal microorganism detection system of claim 1, wherein the temporal correlation comprises a difference between first image information of the wave speckle detected at a first time point and second image information of the wave speckle detected at a second time point different from the first time point.

17. The Intestinal microorganism detection system of claim 16, wherein the first image information and the second image information comprise at least any one of pattern information of the wave speckle and intensity information of the waves.

* * * * *